United States Patent
Saxena et al.

(10) Patent No.: US 6,693,134 B2
(45) Date of Patent: Feb. 17, 2004

(54) BICYCLIC AROMATIC CHEMOKINE RECEPTOR LIGANDS

(75) Inventors: Geeta Saxena, Vancouver (CA); Christopher R. Tudan, Vancouver (CA); Ahmed Merzouk, Richmond (CA); Hassan Salari, Delta (CA)

(73) Assignee: Chemokine Therapeutics Corporation, Vancouver (CA)

( * ) Notice: Subject to any disclaimer, the term of this patent is extended or adjusted under 35 U.S.C. 154(b) by 0 days.

(21) Appl. No.: 09/993,352

(22) Filed: Nov. 13, 2001

(65) Prior Publication Data

US 2003/0045550 A1 Mar. 6, 2003

Related U.S. Application Data

(60) Provisional application No. 60/294,306, filed on May 29, 2001.

(51) Int. Cl.[7] .............................................. A61K 31/38
(52) U.S. Cl. ........................................................ 514/569
(58) Field of Search .............................. 514/543, 544, 514/557, 700, 569

(56) References Cited

U.S. PATENT DOCUMENTS

| | | | | |
|---|---|---|---|---|
| 5,389,684 A | * | 2/1995 | Fairhurst et al. | 514/622 |
| 5,866,545 A | * | 2/1999 | Hagmann et al. | 514/18 |
| 5,932,618 A | * | 8/1999 | Suto et al. | 514/568 |
| 6,403,587 B1 | * | 6/2002 | Kath et al. | 514/249 |

FOREIGN PATENT DOCUMENTS

| | | |
|---|---|---|
| WO | WO 95/05192 | 2/1995 |
| WO | WO 00/02871 | 1/2000 |
| WO | WO 01/00658 | 1/2001 |
| WO | WO 01/05380 | 1/2001 |

* cited by examiner

*Primary Examiner*—James H. Reamer
(74) *Attorney, Agent, or Firm*—Bret E. Field; Bozicevic, Field & Francis

(57) ABSTRACT

The invention provides therapeutic and biological uses of chemokine-receptor-binding compounds (including chemokine receptor ligands such as chemokine receptor agonists or antagonists), such as naphthoic acid derivatives, including uses in the treatment of disease states mediated by chemokines. The relevant chemokine may for example be stromal cell-derived factor (SDF)-1, and the relevant chemokine receptors may for example be corresponding chemokine receptor (CXCR-4). In other aspects, the invention provides corresponding pharmaceutical compositions and therapeutic methods. In one aspect, for example, the invention provides for the use of 3-Hydroxy-2-naphthoic acid in the treatment of disease.

6 Claims, 2 Drawing Sheets

Figure 1. Inhibition of $^{125}$I-SDF-1 Receptor Binding by CTCM226
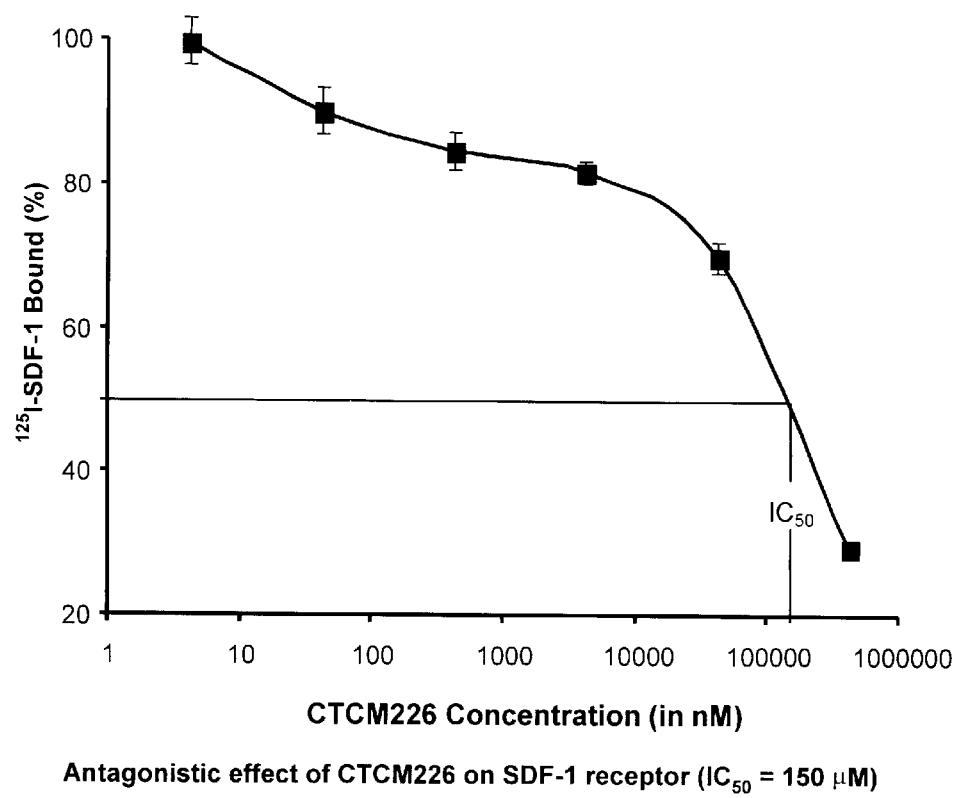
Antagonistic effect of CTCM226 on SDF-1 receptor ($IC_{50}$ = 150 µM)

Figure 2. Inhibition of SDF-1 Induced Calcium Mobilization by CTCM226
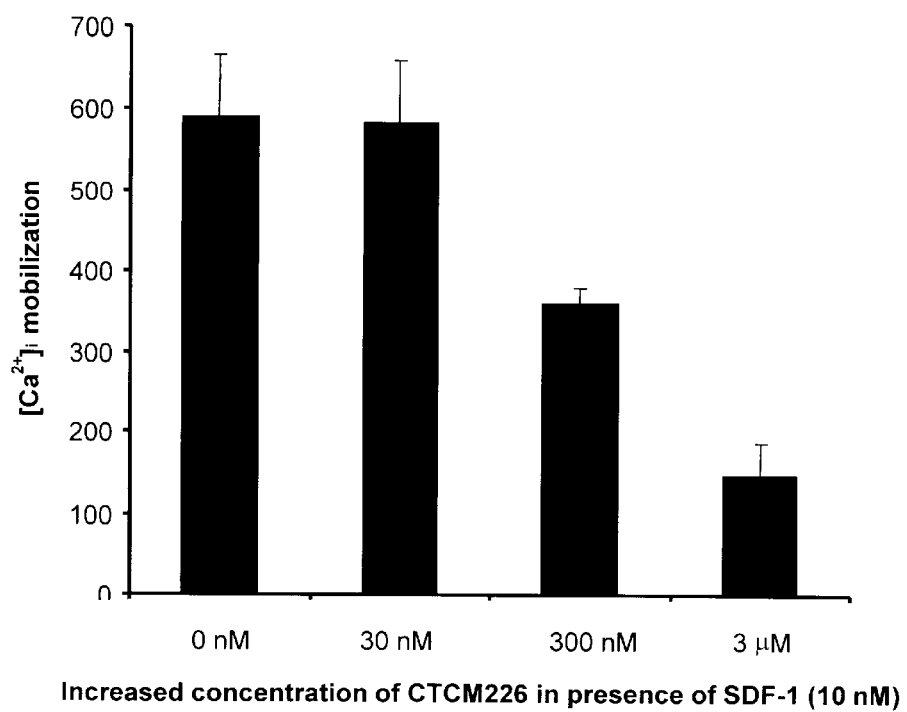

BICYCLIC AROMATIC CHEMOKINE RECEPTOR LIGANDS

FIELD OF THE INVENTION

The invention relates to organic compounds acting as chemokine receptor ligands, including antagonists of CXC chemokine receptor-4 (CXCR-4) and therapeutic uses thereof, such as in the treatment of hematopoietic cells and in the treatment of chemokine or chemokine receptor mediated diseases.

BACKGROUND OF THE INVENTION

Cytokines are soluble proteins secreted by a variety of cells including monocytes or lymphocytes that regulate immune responses. Chemokines are chemotactic cytokines that belongs to a large family of chemoattractant molecules involved in the directed migration of immune cells. They regulate a variety of biological responses and promote the recruitment of multiple lineages of leukocytes and lymphocytes to a specific body organ tissues. The functional role generally assigned to chemokines in the immune process is to elicit mobilization of immune cells against pathogenic organisms by direct recruitment and activation. Based on their structural similarity, chemokines may be subdivided into four subfamilies, CXC, CC, C and $CX_3C$, depending on the position of their first two cysteine residues. SDF-1 belongs to the CXC chemokine family. It exerts its biological activities by binding to a specific cell surface receptor, CXC Chemokine receptor 4 (CXCR-4). In human, CXC chemokine genes are clustered on chromosome 4 (with the exception of SDF-1 gene, which has been localized to chromosome 10) and CC chemokine genes are clustered on chromosome 17.

The molecular targets for chemokines are cell surface receptors CXCR-4, one such receptor is a G protein coupled 7 transmembrane protein, and was previously called LESTR. Majority of chemokine receptors identified to date bind several distinct chemokines at high affinity, with the exception of CXCR-4, which binds only SDF-1. SDF-1 is thought to be the natural ligand for CXCR-4. CXCR-4 is widely expressed on cells of hematopoietic origin, and is a major co-receptor with $CD4^+$ for human immunodeficiency virus 1 (HIV-1). CXCR-4 was found to be overexpressed in glioblastoma multiforme tumor tissue (GMTT), as compared to normal brain tissue (NBT). Expression analysis indicated that CXCR-4 is overexpressed in 57% of the primary glioblastoma tissues and in 8% of the glioblastoma cell lines. Gene-specific RT-PCR analysis indicated that the CXCR-4 gene is overexpressed in several malignant glioma tissues, breast tumor tissues and cell lines. Northern blot analysis indicated expression of CXCR-4 at high levels in certain leukemias, uterine cancer, and Burkitt's lymphoma cell lines. The occipital and temporal lobe showed high levels of CXCR-4 in normal human brain. In adult mouse, CXCR-4 is expressed only in brain, spinal cord, bone marrow, and pituitary gland. Antisense CXCR-4 overexpression in glioblastoma cells caused inhibition of cell proliferation and induction of cellular differentiation in vitro. These findings indicate that CXCR-4 expression may play an important role during embryonic development and also in the genesis of human gliomas; that CXCR-4 plays an important role in the tumorigenic properties of brain, breast, and other tumor types. Its unique expression during mouse development also indicates that CXCR-4 plays an important role in the normal function of brain, spinal cord, and bone marrow during development.

SDF-1 gene occurs in two alternative splicing variants, producing SDF-1 alpha and SDF-1 beta (together referred to herein as SDF-1). The native and genomic amino acid sequences of SDF-1 alpha and SDF-1 beta have been determined.

SDF-1 is functionally distinct from other chemokines in that it is reported to have a fundamental role in the trafficking, exporting and homing of bone marrow progenitor cells. It is also structurally distinct in that it has only about 22% amino acid sequence identity with other CXC chemokines. SDF-1 appears to be produced constitutively by several cell types, and particularly high levels are found in bone-marrow stromal cells. A basic physiological role for SDF-1 is implied by the high level of conservation of the SDF-1 sequence between species. In vitro, SDF-1 stimulates chemotaxis of a wide range of cells including monocytes and bone marrow derived progenitor cells. It also stimulates a high percentage of resting and activated T-lymphocytes.

Chemokines and their receptors determine the distribution of leukocytes within tissues both in healthy and disease states. CXCR-4 and its ligand SDF-1 are found to be involved in the perivascular accumulation of T cells in rheumatoid arthritis. Mast cells are generally considered to be less mobile, residing within tissue sites. However, mast cells increase during inflammation, and are recognized to be important in regulating local neutrophil infiltration. Stimulation of human mast cells with SDF-1 induces a significant increase in intracellular calcium levels. In vitro, SDF-1 mediates dose-dependent migration of human cord blood-derived mast cells and HMC-1 cells across HUVEC monolayer.

SDF-1 is a chemoattractant for CD34(+) progenitor cells, both in vitro and in vivo, and SDF-1 and CXCR-4 are involved in homing of progenitor cells to bone marrow. Experiments indicated that SDF-1 is involved in hematopoiesis, and promotion of the proliferation of human CD34(+) cells purified from normal adult peripheral blood (PB). When CXCR-4 was expressed on PB CD34(+) cells, the amount of CXCR-4 on PB CD34(+) cells was found to be 10 times higher when CD34(+) cells were purified following overnight incubation. CXCR-4 overexpression is correlated with a primitive PB CD34(+) cell subset defined by a CD34(high) CD38(low) CD71(low)c-Kit(low)Thy-1 (+) antigenic profile. The functional significance of CXCR-4 expression was ascertained by the promoting effect of SDF-1a on cell cycle, proliferation, and colony formation. SDF-1 alone increases the percentage of CD34(+) cells in the S+G(2)/M phases and sustains their survival. In synergy with cytokines, SDF-1 increases PB CD34(+) and CD34 (high)CD38(low) cell expansion and colony formation.

A variety of diseases require treatment with agents, which are preferentially cytotoxic to dividing cells. Cancer cells, for example, may be targeted with cytotoxic doses of radiation or chemotherapeutic agents. A significant side-effect of cancer therapy is the pathological impact of such treatments on rapidly dividing normal cells. These normal cells may for example include hair follicles, mucosal cells and the hematopoietic cells, such as primitive bone marrow progenitor cells and stem cells.

Hematopoietic cells that are uncommitted to a final differentiated cell type are defined herein as "progenitor" cells. Hematopoietic progenitor cells possess the ability to differentiate into a variety of cell types directly or indirectly through a particular developmental lineage. Undifferentiated, pluripotent progenitor cells that are not committed to any lineage are referred to herein as "stem cells." All hematopoietic cells can in theory be derived from a single stem cell, which is also able to perpetuate the stem cell lineage as daughter cells become differentiated.

Indiscriminating destruction of hematopoietic cells, such as stem, progenitor or precursor cells, can lead to a reduction in normal mature blood cell counts, such as leukocytes and red blood cells. A major impact on mature cell numbers may be seen particularly with neutrophils (neutropaenia) and platelets (thrombocytopenia), cells which naturally have relatively short half-lives. A decrease in leukocyte count, with concomitant loss of immune system function, may increase a patient's risk of opportunistic infection. Neutropaenia resulting from chemotherapy may for example occur within two or three days of cytotoxic treatments, and may leave the patient vulnerable to infection for up to 2 weeks until the hematopoietic system has recovered sufficiently to regenerate neutrophil counts. A reduced leukocyte count (leukopenia) as a result of cancer therapy may become sufficiently serious that therapy must be interrupted to allow the white blood cell count to rebuild. Interruption of cancer therapy can in turn lead to survival of cancer cells, an increase in the incidence of drug resistance in cancer cells and ultimately in cancer relapse. There is accordingly a need for therapeutic agents and treatments, which facilitate the preservation or regeneration of hematopoietic cell populations in cases where the number of such cells has been reduced due to disease or to therapeutic treatments such as radiation and chemotherapy.

Bone marrow transplantation has been used in the treatment of a variety of hematological, autoimmune and malignant diseases. In conjunction with bone marrow transplantation, ex vivo hematopoietic (bone marrow) cell culture may be used to expand the population of hematopoietic cells, particularly progenitor or stem cells, prior to reintroduction of such cells into a patient. In ex vivo gene therapy, hematopoietic cells may be transformed in vitro prior to reintroduction of the transformed cells into the patient. In gene therapy, using conventional recombinant DNA techniques, a selected nucleic acid, such as a gene, may be isolated, placed into a vector, such as a viral vector, and the vector transfected into a hematopoietic cell, to transform the cell, and the cell may in turn express the product coded for by the gene.

The cell may then be introduced into a patient. Hematopoietic stem cells were initially identified as a prospective target for gene therapy. However, problems have been encountered in efficient hematopoietic stem cell transfection. There is accordingly a need for agents and methods, which may facilitate the proliferation of hematopoietic cells in ex vivo cell culture. There is also a need for agents that may be used to facilitate the establishment and proliferation of engrafted hematopoietic cells that have been transplanted into a patient.

A number of proteins have been identified as stimulators of hematopoietic cell proliferation (some of which are identified as hematopoietic growth factors). Cytokines involved in the induction of differentiation or proliferation of hematopoietic cells, particularly progenitor cells, include the following: G-CSF (granulocyte colony stimulating factor); LIF (leukemia inhibitory factor) and GM-CSF (granulocyte-macrophage colony stimulating factor).

The alpha Chemokine CXCR-4 and its ligand SDF-1 are postulated to be important in the development of the B-cell arm of the immune system. CXCR-4 is a critical coreceptor in support of viral entry by T-cell line tropic strains (X4) of the Human Immunodeficiency Virus Type 1 (HIV-1), viral variants, which predominate in some infected individuals in end stage disease. SDF-1 blocks X4-tropic HIV-1 infection of CD4+target cell in vitro, and allelic variants of the human gene encoding SDF-1 in vivo correlate with delayed disease progression. Thus, CXCR-4 may be an appropriate target for therapeutic intervention in acquired immunodeficiency syndrome (AIDS).

The localization of chronic lymphocytic leukemia (CLL) B-cells in bone marrow is not a adhesion phenomenon but a crucial step for their survival. SDF-1 produced by bone marrow stromal cells plays an important role in B-lymphocyte development and trafficking. It is found that Chemokine system SDF-1/CXCR-4 plays an important role in the accumulation of CLL B-cells.

Prostate neoplasm has a striking tendency to metastasize or "home" to bone. Metastases occur, when malignant cells escape from the primary tumor, penetrate and circulate through the bloodstream and subsequently arrest in the target tissues. It is found that metastatic prostate carcinoma utilizes the SDF-1/CXCR-4 pathway to localize to the bone marrow. Studies indicate that prostate cancers and perhaps other neoplasms (i.e. breast) may use the SDF-1/CXCR-4 pathway during their hematogenous spread to bone.

SUMMARY OF THE INVENTION

In various aspects, the invention provides methods for the use of chemokine-receptor-binding compounds (which may be chemokine receptor ligands such as chemokine receptor agonists or antagonist), and/or salts thereof, in treating chemokine mediated diseases or chemokine receptor mediated diseases, such as SDF-1 mediated diseases, or diseases mediated by chemokine receptors CXCR-4.

In some embodiments, the invention relates to methods of using a compound of formula (I), or a pharmaceutically acceptable salt thereof, to formulate a medicament for the treatment of a chemokine mediated disease state, or to treat such a disease:

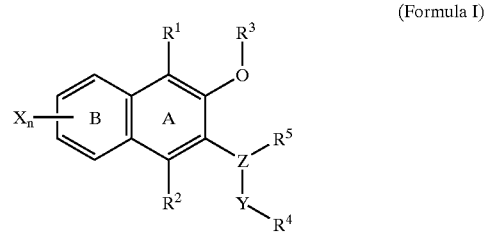

(Formula I)

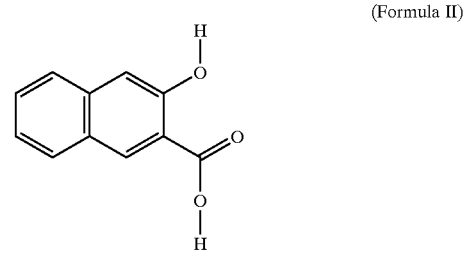

(Formula II)

3-Hydroxy-2-naphthoic acid

-continued (Formula III)

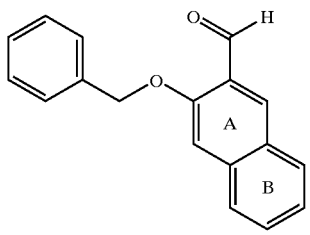

3-Benzyloxy-naphthalene-2-carboxaldehyde (Formula IV)

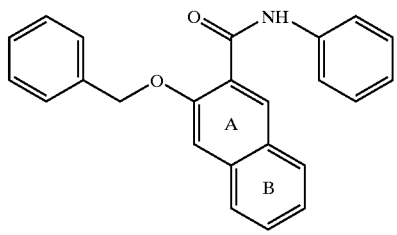

3-Benzyloxy-3-(2-imidazolyl)naphthalene (Formula V)

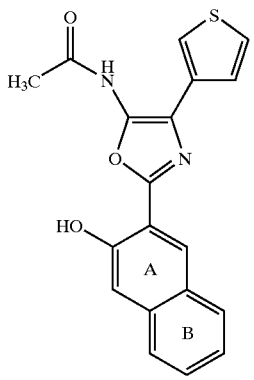

2-(2-(3-hydroxy)naphthyl)-4-(3-thiophenyl)-5-acetamidooxazole (Formula VI)

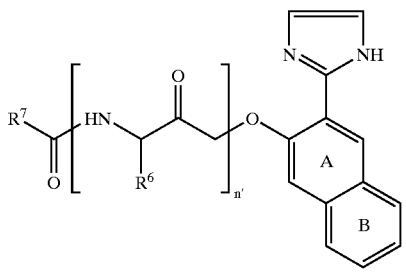

N-Allyloxy carbonyl-3-amino-5-(3-imidazolyl-2-naphthyloxy)-4-oxopentanoic acid (Formula VII)

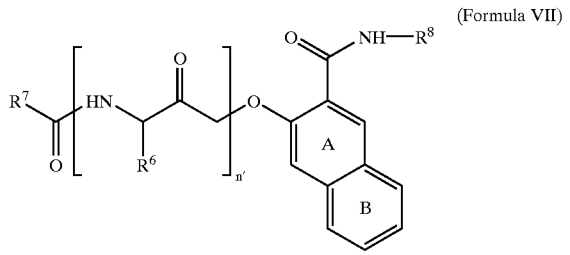

In some embodiments, ring A may be aromatic and may be heterocyclic with one or more heteroatoms selected from the group consisting of oxygen and nitrogen. In Formula I, Ring B may be aromatic or non-aromatic, may be heterocyclic with one or more heteroatoms selected from the group consisting of oxygen and nitrogen , "x" may for example represent a substitution at any position in ring B (in accordance with the presence or absence of hetroatom) where the substituents may be from the group consisting of hydrogen, hydroxyl, methoxy, carboxyl, esters (alkyl, phenyl or benzyl) alkyl, alkenyls, alkynyls, amino, amido, thio, thiazolo, imidazolo or may be fatty acids.

In alternative embodiments, $R_1$ and $R_2$ at each occurance may independently be selected from substituents having 50 or fewer atoms, wherein the substituent may be selected from the group consisting of: hydrogen, cyano, nitro, amino, sulfonyls, methoxy and fluoro; and combinations thereof.

In alternative embodiments, $R_3$, $R_4$, $R_5$, $R_6$, $R_7$ and $R_8$ at each occurance may independently be selected from substituents having 30 or fewer atoms, wherein the substituent may be selected from the group consisting of: H; substituted or unsubstitued alkyls, such as $C_{1-5}$ alkyls; substituted or unsubstitued cycloalkyls, such as $C_{3-5}$ cycloalkyls; substituted or unsubstitued alkenyls, such as $C_{2-5}$ alkenyls; substituted or unsubstitued alkynyls, such as $C_{2-6}$ alkynyls; substituted or unsubstitued aryls; such as benzyl and benzyl esters; substituted or unsubstitued heterocycles; hydroxyls; aminos; nitros; thiols; primary, secondary or tertiary amines; imines; amides; imidos, imidazoles; thiazoles; phosphonates; phosphines; carbonyls; carboxyls; silyls; ethers; thioethers; sulfonyls; sulfonates; selenoethers; ketones; aldehydes; esters; —$CF_3$; —CN; amino acids, long chain amino acids, fatty acids and combinations thereof.

In formula I, "X" represents substitution in ring 'B' at any position, where 'n' may be 0 or an integer from 1 to 4. "Y" may be a variable group, representing 'O' (oxygen) or 'N' (nitrogen). "Z" may be an $sp^2$ carbon that may be part of a functional group as follows:

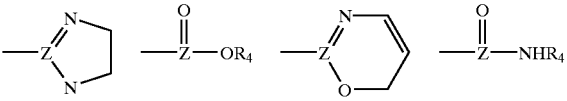

For compounds of formula I, VI and VII, "n" may be 0 or an integer from 1 to 4 and "n'" may be 0 or an integer from 1 to 4.

In some embodiments, the chemokine may be selected from the group consisting of: SDF-1, and chemokines that bind to CXCR-4.

In various embodiments, the invention provides for the use of compounds of the invention in the treatment of diseases selected from the group consisting of inflammation, chronic and acute inflammation, arthritis, rheumatoid arthritis, osteoarthritis, ARDS, psoriasis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, sickle cell disease, ulcerative colitis, septic shock, endotoxic shock, urosepsis, glomerulonephritis, lupus nephritis, thrombosis, graft vs. host disease, angiogenesis, NSCLC, human ovarian cancer, human pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, uterine carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma, tumors of the brain, tumors of the nerves, tumors of the eyes, tumors of the meninges, astrocytomas, gliomas, malignant gliomas, glioblastomas, retinoblastomas, neuromas, neuroblastomas, Schwannomas, meningiomas, solid tumors arising from hematopoietic malignancies (such as leukomias, chloromas, plasmacytomas, and the plaques and tumors of mycosis fungoides and cutaneous T-cell lymphoma/leukemia), solid tumors arising from lymphomas, non Hodgkin's lymphoma (NHL), diseases relating to abnormal proliferation of hematopoietic cells, hematopoietic stemcytopenia after bone marrow transplantation, leukocytopenia, neutropenia, thromocytopenia, leukopenia, lymphopenia after chemotherapy, ex vivo gene therapy in bone marrow transplant and/or blood transufion, in the treatment of hematopoietic progenitor and stem cell proliferation and migration disorders, antiviral infections, HIV, AIDS, and neurodegenerative diseases such as Alzheimer, Parkinson's, multiple sclerosis, disorder of bone metabolism such as osteoporesis.

In accordance with various aspects of the invention, CXCR4 antagonists may be used to treat hematopoietic cells, for example to increase the rate of hematopoietic stem or progenitor cellular multiplication, self-renewal, expansion, proliferation, or peripheralization. In various aspects, the invention relates to methods of promoting the rate of hematopoietic cell multiplication, which encompases processes that increase and/or maintain cellular multiplication, self-renewal, expansion, proliferation or peripheralization. This may for example be useful in some embodiments for in vitro hematopoietic cell cultures used in bone marrow transplantation, peripheral blood mobilization, or ex vivo expansion. CXCR4 antagonists may also be used therapeutically to stimulate hematopoietic cell multiplication, self-renewal, expansion, proliferation or peripheralization in vivo, for example in some embodiments involving human diseases such as a cancer or an autoimmune disease. The hematopoietic cells targeted by the methods of the invention may include hematopoietic progenitor or stem cells.

In alternative embodiments, CXCR4 antagonists may be used to treat a variety of hematopoietic cells, and such cells may be isolated or may form only part of a treated cell population in vivo or in vitro. Cells amenable to treatment with CXCR4 antagonists may for example include cells in the hematopoietic lineage, beginning with pluripotent stem cells, such as bone marrow stem or progenitor cells, lymphoid stem or progenitor cells, myeloid stem cells, CFU-GEMM cells (colony-forming-unit granulocyte, erythroid, macrophage, megakaryocye), B stem cells, T stem cells, DC stem cells, pre-B cells, prothymocytes, BFU-E cells (burst-forming unit—erythroid), BFU-MK cells (burst-forming unit—megakaryocytes), CFU-GM cells (colony-formng unit—granulocyte-macrophage), CFU-bas cells (colony-forming unit—basophil), CFU-Mast cells (colony forming unit—mast cell), CFU-G cells (colony forming unit granulocyte), CFU-M/DC cells (colony forming unit monocyte/dendritic cell), CFU-Eo cells (colony forming unit eosinophil), CFU-E cells (colony forming unit erythroid), CFU-MK cells (colony forming unit megakaryocyte), myeloblasts, monoblasts, B-lymphoblasts, T-lymphoblasts, proerythroblasts, neutrophillic myelocytes, promonocytes, or other hematopoietic cells that differentiate to give rise to mature cells such as macrophages, myeloid related dendritic cells, mast cells, plasma cells, erythrocytes, platelets, neutrophils, monocytes, eosinophils, basophils, B-cells, T-cells or lymphoid related dendritic cells.

In some embodiments, the invention provides methods of increasing the circulation of hematopoietic cells by mobilizing them from the marrow to the peripheral blood comprising administering an effective amount of a CXCR4 antagonist to hematopoietic cells of a patient undergoing autologous mobilization where hematopoietic stem/progenitor cells may be mobilized into the peripheral blood (1) during the rebound phase of the leukocytes and/or platelets after transient granulocytopenia and thrombocytopenia induced by myelosuppressive chemotherapy, (2) by hematopoietic growth factors, or (3) by a combination of both. Such treatment may for example be carried out so as to be effective to mobilize the hematopoietic cells from a marrow locus (i.e. a location in the bone marrow) to a peripheral blood locus (i.e. a location in the peripheral blood). Such treatments may for example be undertaken in the context of or for the clinical procedure of leukapheresis or apheresis. In alternative embodiments, CXCR4 antagonists may be used in ex vivo stem cell expansion to supplement stem cell grafts with more mature precursors to shorten or potentially prevent hematopoietic cell depletion, including conditions such as pancytopenia, granulocytopenia, thrombocytopenia, anemia or a combination thereof; to increase the number of primitive progenitors to help ensure hematopoietic support for multiple cycles of high-dose therapy; to obtain sufficient number of stem cells from a single marrow aspirate or apheresis procedure, thus reducing the need for large-scale harvesting of marrow of multiple leukopheresis; to generate sufficient cells from a single cord-blood unit to allow reconstitution in an adult after high-dose chemotherapy; to purge stem cell products of contaminating tumour cells; to generate large volumes of immunologically active cells with antitumour activity to be used in immunotherapeutic regimens or to increase the pool of stem cells that could be targets for the delivery of gene therapy.

In alternative embodiments, the invention provides methods to enrich CD34+progenitor cells which are utilized in bone marrow (BM) and peripheral blood (PB) stem cell transplantation, wherein the hematopoietic stem cell transplantation (HSCT) protocols may for example be utilized for the purpose of treating the following diseases (from Ball, E. D., Lister, J., and Law, P. Hematopoietic Stem Cell Therapy, Chruchill Livingston (of Harcourt Inc.), New York (2000)): Aplastic Anemia; Acute Lymphoblastic Anemia.; Acute Myelogenous Leukemia; Myelodysplasia; Multiple Myeloma; Chronic Lymphocytic Leukemia; Congenital Immunodeficiencies (such as Autoimmune Lymphoproliferative disease, Wiscott-Aldrich Syndrome, X-linked Lymphoproliferative disease, Chronic Granulamatous disease, Kostmann Neutropenia, Leukocyte Adhesion Deficiency); Metabolic Diseases (for instance those which have been HSCT indicated such as Hurler Syndrome (MPS I/II), Sly Syndrome (MPS VII), Chilhood onset cerebral X-adrenoleukodystrophy, Globard_cell Leukodystrophy).

In alternative embodiments, the invention relates to the use as CXCR4 antagonists of compounds of Formula I, with the exception of one or more of the compounds of formulae II or III or IV or V or VI or VII.

BRIEF DESCRIPTION OF THE DRAWINGS

FIG. 1 shows the inhibitory effect of 3-Hydroxy-2-naphthoic acid (designated herein as CTCM226) on the binding of SDF-1 to CXCR-4 receptor.

FIG. 2 shows Inhibition effect of CTCM226 on SDF-1 induced [Ca+$^{+2}$] mobilization.

DETAILED DESCRIPTION OF THE INVENTION

In some embodiments, the compounds of the invention may have a specific chemokine receptor binding affinity (IC$_{50}$) below 1 mM, below 500 uM, below 200 uM, below 100 uM, below 50 uM, below 10 uM, below 1000 nM, below 100 nM, below 50 nM, below 10 nM or below 1 nM; and may have a selective affinity for a selected chemokine receptor, such as a 10-fold selective affinity, a 50-fold selective affinity or a 100-fold selective affinity, for a selected chemokine receptor relative to an alternative chemokine receptor. For example, in some embodiments, the compounds may have a binding affinity for CXCR-4 of below 1 mM, below 500 uM, below 200 uM, below 100 uM, below 50 uM, below 10 uM, below 1000 nM, below 100 nM, below 50 nM, below 10 nM or below 1 nM. Receptor binding affinities may by assayed by any of a number of standard methods, such as competitive displacement of radioactively labeled ligands.

In various aspects, the invention relates to compounds having alternative substitutions and substituent groups, designated in formulae herein as "R", typically with a numeric superscript to identify the substituent group. A substituent group is generally a group that replaces one or more hydrogen atoms attached to a parent structure. The organic substituent groups are for example identified in the Handbook of Chemistry and Physics, 79th Edition, CRC Press (all of which are hereby incorporated by reference). Substituent groups of the invention may for example be selected from groups having from 1 to 100 atoms, such as groups having 100 or fewer, 50 or fewer, 25 or fewer, 20 or fewer, 15 or fewer, 10 or fewer, 5 or fewer, 4, 3, 2, or 1 atom(s). Atoms in such substituents may for example be selected from the group consisting of carbon, hydrogen, oxygen, nitrogen, halogen, sulfur, silicon, arsenic, boron, selenium and phosphorus.

Substituent groups may for example be substituted or unsubstitued alkyls, such as, C$_{1-10}$ alkyls, C$_{1-6}$ alkyls; substituted or unsubstitued cycloalkyls, such as C$_{1-10}$ cycloalkyls, C$_{3-6}$ cycloalkyls; substituted or unsubstitued alkenyls, such as C$_{1-10}$ alkenyls, C$_{2-6}$ alkenyls; substituted or unsubstitued alkynyls, such as C$_{1-10}$ alkynyls, C$_{2-6}$ alkynyls; substituted or unsubstitued aryls; substituted or unsubstitued heterocycles; hydroxyls; aminos; nitros; thiols; primary, secondary or tertiary amines; imines; amides; imides, amino acids; amino esters; phosphonates; phosphines; carbonyls; carboxyls; silyls; ethers; thioethers; sulfonyls; sulfonates; selenoethers; ketones; aldehydes; esters; —CF$_3$; —CN; imidazoles; thiazoles; pyrazoles; and combinations thereof. Substituent groups which are themselves substituted may be substituted with similar substituents.

In some embodiments, a substituent group may comprise a cyclic, heterocyclic or polycyclic group. The term "cyclic group", as used herein, includes cyclic saturated or unsaturated (optionally aromatic) group having from 3 to 10, 4 to 8, or 5 to 7 carbon atoms. Exemplary cyclic groups include cyclopropyl, cyclobutyl, cyclopentyl, cyclohexyl, and cyclooctyl. Cyclic groups may be unsubstituted or substituted at one or more ring positions. A cyclic group may for example be substituted with halogens, alkyls, cycloalkyls, alkenyls, alkynyls, aryls, heterocycles, hydroxyls, aminos, nitros, thiols, pyroles; imidazoles; thiazoles; pyrazoles; amines, imines, amides, amino acids, amino esters; phosphonates, phosphines, carbonyls, carboxyls, silyls, ethers, thioethers, sulfonyls, sulfonates, selenoethers, ketones, aldehydes, esters, —CF$_3$, —CN.

The term "heterocyclic group" includes cyclic saturated, unsaturated and aromatic groups having from 3 to 10, 4 to 8, or 5 to 7 carbon atoms, wherein the ring structure includes about one or more heteroatoms. Heterocyclic groups may include pyrane, pyrone, pyrrolidine, oxolane, thiolane, imidazole, oxazole, pyrazole, thiazole, piperidine, piperazine, morpholine. The heterocyclic ring may be substituted at one or more positions with such substituents as, for example, halogens, alkyls, cycloalkyls, alkenyls, alkynyls, aryls, other heterocycles, hydroxyl, amino, nitro, thiol, amines, imines, amides, amino acids, amino esters, phosphonates, phosphines, carbonyls, carboxyls, silyls, ethers, thioethers, sulfonyls, selenoethers, ketones, aldehydes, esters, —CF$_3$, —CN. Heterocycles may also be bridged or fused to other cyclic groups as described below.

The term "polycyclic group" as used herein is intended to refer to two or more saturated, unsaturated or aromatic cyclic rings in which two or more carbons are common to two adjoining rings, so that the rings are "fused rings". Rings that are joined through non-adjacent atoms may be termed "bridged" rings. Each of the rings of the polycyclic group may be substituted with such substituents as described above, as for example, halogens, alkyls, cycloalkyls, alkenyls, alkynyls, hydroxyl, amino, nitro, thiol, amines, imines, amides, esters, phosphonates, phosphines, carbonyls, carboxyls, silyls, ethers, thioethers, sulfonyls, selenoethers, ketones, aldehydes, esters, —CF$_3$, or —CN.

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl has 20 or fewer carbon atoms in its backbone (C$_1$–C$_{20}$ for straight chain, C$_3$–C$_{20}$ for branched chain), or 10 or fewer carbon atoms. In some embodiments, cycloalkyls may have from 4–10 carbon atoms in their ring structure, such as 5, 6 or 7 carbon rings. Unless the number of carbons is otherwise specified, "lower alkyl" as used herein means an alkyl group, as defined above, having from one to ten carbon atoms in its backbone structure. Likewise, "lower alkenyl" and "lower alkynyl" have chain lengths often or less carbons.

The term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group. Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkyloxycarbonyl", as used herein, refers to the group —C(O)—O-alkyl, and the term "aryloxycarbonyl" refers to —C(O)—O-aryl. The term "acyloxy" refers to —O—C(O)-R$_7$, in which R$_7$ is alkyl, alkenyl, alkynyl, aryl, aralkyl or heterocyclyl.

The term "amino", as used herein, refers to —N(R)(R), in which R and R are each independently hydrogen, alkyl, alkenyl, alkynyl, aralkyl, aryl, or in which R and R together with the nitrogen atom to which they are attached form a ring having 4–8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N(R$_8$)(R$_9$), in which R$_8$ and R$_9$ are as defined above. The term "acylamino" refers to —N(R'$_8$)C(O)-R$_7$, in which R$_7$ is as defined above and R'$_8$ is alkyl.

The term "amino acids", as used herein, refers to —CH(N$^+$H$_3$)COO$^-$, in which a substitution could be at either or both 'C' and 'N' positions.

The term "amino acid esters", as used herein, refers to —CH(NHCOOR$_{10}$)COO—; where R$_{10}$ is defined as above.

As used herein, the term "nitro" means —NO$_2$; the term "halogen" designates —F, —Cl, —Br or —I; the term "sulthydryl" means —SH; and the term "hydroxyl" means —OH.

The term "aryl" as used herein includes 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —CF$_3$, —CN, or the like. Aryl groups can also be part of a polycyclic group. For example, aryl groups include fused aromatic moieties such as naphthyl, anthracenyl, quinolyl, indolyl, and the like.

With reference to FIG. 3 in one aspect, the compounds of the invention may comprise two hydrophobic aromatic rings, A and B, in which one ring or both the rings can be substituted at different positions as shown in ring A in FIG. 3. In some embodiments, substitutions may be made to the hydrophobic aromatic rings that preserve the hydrophobic and aromatic characteristic of the rings, such as the substitution of heteroatoms within the ring or exocyclic substituents. Similarly, substitutions may be made at different positions such as hydroxyl at C3 and carboxylic at C2 in ring A.

In one aspect, the present invention relates to uses of a naphthoic acid derivative designated herein as 3-Hydroxy-2-naphthoic acid;

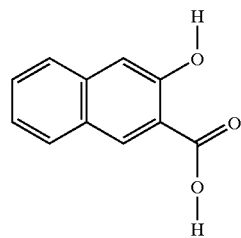

3-Hydroxy-2-naphthoic acid (Compound 1); [CAS 92-70-6]

Molecular Formula: C$_{11}$H$_8$O$_3$

Molecular Weight: 188.18

EXAMPLES

The following examples are illustrative of various aspects of the invention.

Synthesis:

The 3-Hydroxy-2-naphthoic acid (Compound 1, CAS number 92-70-6) is commercially available and may also be prepared in a variety of ways known to those skilled in the art. For example, naphthalene, commonly known as tar camphor, containing ring A and B, is a natural chemical that can be isolated from dry coal tar. This may be used as a starting analog to synthesize 3-hydroxy-2-naphthoic acid via oxidation and then treating beta-naphthol with CO$_2$ under pressure to yield compound 1.

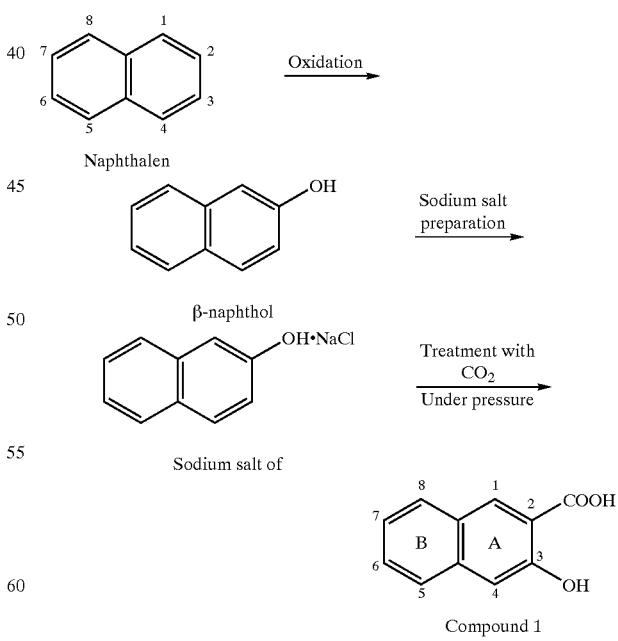

Alternative compounds of the invention may be synthesized using known methods, such as methods disclosed in International Patent Publication WO 00/02871 published Jan. 20, 2000 and U.S. Pat. No. 5,866,545 issued to Hagmann et al. on Feb. 2, 1999, for the synthesis of 2-(2-(3-hydroxy)naphthyl)-4-(3-thiophenyl)-5-acetamidooxazole).

Receptor Binding

This example discloses the ability of compounds of the invention, such as naphthoic acid derivatives, such as CTCM226 (1), to inhibit binding of SDF-1 to CXCR-4 receptor. The binding studies were conducted using $I^{125}$ labeled SDF-1 as competitor ligand. FIG. 1 shows the inhibitory effect of compound (1) on the binding of SDF-1 to CXCR-4 receptor. The $IC_{50}$ was evaluated at 150 uM.

Calcium Release

A rapid, transient rise in the free cytosolic $Ca^{2+}$ concentration ($[Ca^{2+}]_i$) is one of the events associated with the Chemokine mediated induction of the associated receptors and is assumed to be involved in many of the subsequent cellular reactions. Both $Ca^{2+}$ release from intracellular stores and $Ca^{2+}$ influx from the extracellular space contribute to the rise in $[Ca^{2+}]_i$. FIG. 2 shows the inhibition of SDF-1 induced intracellular $[Ca^{2+}]_i$ mobilization by CTCM226 in THP-1 cells. Fura-2,AM loaded THP-1 cells were incubated with CTCM226 for 60 min prior to induction of $[Ca^{2+}]_i$ mobilization by 10 nM SDF-1. Results illustrate the effect of CTCM226 (1) on SDF-1 induced $Ca^{2+}$ mobilization.

Compound 1 showed an inhibition of SDF-1 induced $[Ca^{2+}]_i$ mobilization in THP-1 cells to concentration to 3 uM where the $IC_{50}$ was evaluated to be 600 nM. In accordance with this aspect of the invention, the naphthoic acid derivative, such as compound 1 or corresponding salts may be used for the treatment of a wide range of inflammatory diseases such as gout, arthritis, osteoarthritis, rheumatoid arthritis, and ARDS.

Therapeutic Formulations

In one aspect, the invention provides a variety of therapeutic uses for naphthoic acid derivative, such as compound (1). In various embodiments, the compounds of the invention may be used therapeutically in formulations or medicaments for the treatment of CXCR-4 mediated diseases. The invention provides corresponding methods of medical treatment, in which a therapeutic dose of a compound of the invention is administered in a pharmacologically acceptable formulation. Accordingly, the invention also provides therapeutic compositions comprising compounds of the invention and a pharmacologically acceptable excipient or carrier. The therapeutic composition may be soluble in an aqueous solution at a physiologically acceptable pH.

The invention provides pharmaceutical compositions (medicaments) containing (comprising) compound of the invention. In one embodiment, such compositions include compound of the invention in an effective amount, meaning a therapeutically or prophylactically effective amount, sufficient to modulate CXCR-4 activity, and a pharmaceutically acceptable carrier. In other embodiments, the compositions of the invention may include compound of the invention in a therapeutically or prophylactically effective amount sufficient to modulate the activity SDF-1, and a pharmaceutically acceptable carrier. Compounds of the invention may also be used in combination with other compositions and procedures for the treatment of diseases.

A "therapeutically effective amount" refers to an amount effective, at dosages and for periods of time necessary, to achieve the desired therapeutic result, such as modulation of CXCR-4 or SDF-1 activity. A therapeutically effective amount of a compound of the invention may vary according to factors such as the disease state, age, sex, and weight of the individual, and the ability of compounds of the invention to elicit a desired response in the individual. Dosage regimens may be adjusted to provide the optimum therapeutic response. A therapeutically effective amount is also one in which any toxic or detrimental effects of compounds of the invention are outweighed by the therapeutically beneficial effects.

A "prophylactically effective amount" refers to an amount effective, at dosages and for periods of time necessary, to achieve the desired prophylactic result, such as modulation of CXCR-4, SDF-1 activity. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

In particular embodiments, a preferred range for therapeutically or prophylactically effective amounts of compounds of the invention may be 0.1 nM -0.1 M, 0.1 nM -0.05M, 0.05 nM -10 1M or 0.01 nM -100 1M. Alternatively, total daily dose may range from about 0.001 to about 100 mg/kg, or up to 10 mg/kg or up to 1 mg/kg of patients body mass. Dosage values may vary with the severity of the condition to be alleviated. It is to be further understood that for any particular subject, specific dosage regimens should be adjusted over time according to the individual need and the professional judgement of the person administering or supervising the administration of the compositions, and that dosage ranges set forth herein are exemplary only and are not intended to limit the scope or practice of the methods of the invention.

The amount of a compound of the invention in a therapeutic composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, compounds of the invention can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating compounds of the invention in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, compounds of the invention may be formulated with one or more additional compounds that enhance the solubility of compounds of the invention.

Pharmaceutically acceptable salts include salts that are well known to those skilled in the art such as basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, alicylic acid, phenylacetic acid and mandelic acid. In alternative embodiments, pharmaceutically acceptable cation salts may include alkaline, alkaline earth, ammonium and quaternary ammonium cations.

In accordance with another aspect of the invention, therapeutic compositions of the present invention, comprising compound of the invention, may be provided in containers having labels that provide instructions for use of compounds of the invention to treat chemokine or chemokine receptor mediated diseases, inflammation, chronic and acute inflammation, arthritis, rheumatoid arthritis, osteoarthritis, ARDS, psoriasis, allograft rejection, chronic transplant rejection, asthma, atherosclerosis, mononuclear-phagocyte dependent lung injury, idiopathic pulmonary fibrosis, sarcoidosis, focal ischemia, atopic dermatitis, chronic obstructive pulmonary disease, sickle cell disease, ulcerative colitis, septic shock, endotoxic shock, urosepsis, glomerulonephritis, thrombosis, graft vs. host disease, angiogenesis, NSCLC, human ovarian cancer, human pancreatic adenocarcinoma, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, uterine carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma.

An alternative aspect of the invention, chemokine or chemokine receptor mediated diseases may include cancers susceptible to anti-angiogenic treatment, including both primary and metastatic solid tumors, including carcinomas of breast, colon, rectum, lung, orpharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). In some aspects of the invention, compounds of the invention may also be useful in treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas), diseases relating to abnormal proliferation and/or migration of hematopoietic cells, hematopoietic stemcytopenia after bone marrow transplantation, leukocytopenia, neutropenia, thromocytopenia, leukopenia, lymphopenia after chemotherapy, ex vivo gene therapy in bone marrow transplant and/or blood transfusion, antiviral infections, HIV, AIDS, and neurodegenerative diseases such as Alzheimer, Parkinson's, multiple sclerosis, disorder of bone metabolism such as osteoporesis.

In addition, compounds of the invention may be useful in the prevention of metastases from the tumors described above either when used alone or in combination with radiotherapy and/or other chemotherapeutic agents.

Conclusion

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

What is claimed is:

1. A method of treating a chemokine mediated disease state, or a disease state mediated by a receptor of the chemokine, in a mammal in need of such treatment, which comprises administering to the mammal an effective amount of a compound of Formula (I), or a pharmaceutically acceptable salt thereof:

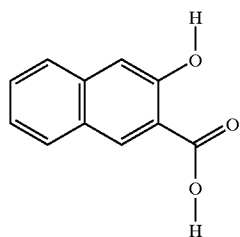

(I)

and,
wherein the chemokine is selected from the group consisting of: SDF-1 and chemokines that bind to CXCR-4.

2. A method of modulating the activity of a chemokine or a receptor of the chemokine in a host, comprising administering to the host an effective amount of a compound of Formula (I):

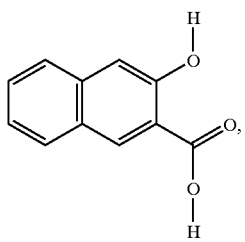

(I)

or a pharmaceutically acceptable salt thereof;

wherein the chemokine is selected from the group consisting of: SDF-1 and chemokines that bind to CXCR-4.

3. A method of inhibiting the interaction of a chemokine with a receptor of the chemokine in a mammal, comprising administering to the mammal an effective amount of a compound of Fformula (I), or a pharmaceutically acceptable salt thereof:

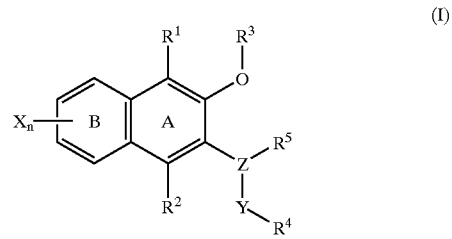

(I)

wherein the chemokine is selected from the group consisting of: SDF-1 and chemokines that bind to CXCR-4.

4. The method of any one of claims 1 to 3, wherein the compound binds to the receptor of the chemokine with a binding affinity below 100 nM.

5. The method of any one of claims 1 to 3, wherein the chemokine mediated disease is selected from the group consisting of glioblastoma, glioma, breast cancer, prostate cancer, Burkitt's lymphoma, uterine cancer, leukemia, metastases, HIV-1 infection, and rheumatoid arthritis.

6. A pharmaceutical composition or a pharmaceutically acceptable salt thereof, and a pharmaceutically acceptable carrier, excipient or diluent, for use in the method of any one of claims 1–3, wherein the compound has the following formula:

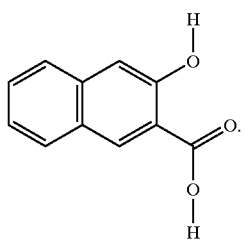

* * * * *

UNITED STATES PATENT AND TRADEMARK OFFICE
CERTIFICATE OF CORRECTION

PATENT NO.   : 6,693,134 B2
DATED        : February 17, 2004
INVENTOR(S)  : Saxena Geeta et al.

It is certified that error appears in the above-identified patent and that said Letters Patent is hereby corrected as shown below:

Column 18,
Lines 10-20, delete Formula in Claim 3, to be replaced with

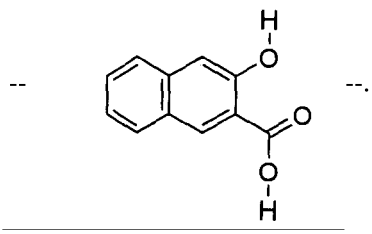

Line 7, the word "Fformula" should read -- Formula --

Signed and Sealed this

Fourteenth Day of September, 2004

JON W. DUDAS
*Director of the United States Patent and Trademark Office*